(12) United States Patent
Monteleone et al.

(10) Patent No.: US 7,026,279 B2
(45) Date of Patent: Apr. 11, 2006

(54) USE OF 3-(METHOXYMETHYL)-2-PENTYLCYCLOPENTA DERIVATIVES IN PERFUME COMPOSITIONS

(75) Inventors: Michael G. Monteleone, Cliffwood Beach, NJ (US); Matthew John Clements, Old Bridge, NJ (US); Louis Croce, Jr., Middletown, NJ (US); Robert P. Belko, Monroe, NJ (US); Manfred Pawlak, Princeton, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/875,752

(22) Filed: Jun. 24, 2004

(65) Prior Publication Data

US 2005/0288210 A1 Dec. 29, 2005

(51) Int. Cl.
*A61Q 13/00* (2006.01)
(52) U.S. Cl. .................. 512/26; 512/27; 568/379
(58) Field of Classification Search .................. 512/27, 512/26; 568/379
See application file for complete search history.

(56) References Cited

U.S. PATENT DOCUMENTS

| | | | |
|---|---|---|---|
| 3,951,876 A | * | 4/1976 | Celli et al. ............... 512/6 |
| 3,981,891 A | * | 9/1976 | Celli et al. ............... 549/341 |
| 4,308,179 A | | 12/1981 | Celli |
| 4,499,297 A | | 2/1985 | Rautenstrauch |
| 4,534,891 A | | 8/1985 | Boden et al. |
| 5,300,489 A | | 4/1994 | Boden et al. |
| 6,303,798 B1 | | 10/2001 | Belko et al. |
| 6,632,788 B1 | | 10/2003 | Levorse, Jr. et al. |

* cited by examiner

*Primary Examiner*—Monique T. Cole
(74) *Attorney, Agent, or Firm*—Joseph F. Leightner; Elizabeth M. Quirk

(57) ABSTRACT

3-(methoxymethyl)-2-pentylcyclopent derivative compounds having the structure set forth below are disclosed:

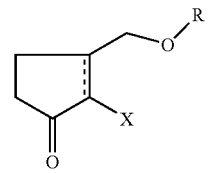

where:
the dotted line represents a potential double bond;
R is selected from methyl and ethyl; and
X is a $C_1$–$C_7$ hydrocarbon moiety.

These compounds are useful fragrance chemicals, suitable for use in creating fragrances and scents in items such as perfumes, colognes and personal care products.

12 Claims, No Drawings

USE OF 3-(METHOXYMETHYL)-2-PENTYLCYCLOPENTA DERIVATIVES IN PERFUME COMPOSITIONS

FIELD OF THE INVENTION

The use 3-(methoxymethyl)-2-pentylcyclopenta derivatives are disclosed as fragrance chemicals suitable for incorporation in fine fragrances, cosmetics, toiletries, and related applications.

BACKGROUND OF THE INVENTION

There is an ongoing need in the fragrance industry to provide new chemicals to give perfumers and others the ability to create new fragrances for perfumes, colognes and personal care products. Various commercially successful fragrance materials are known in the art including those described in U.S. Pat. Nos. 6,303,798 and 6,632,788.

Despite these and other disclosures there is an ongoing need for the development of new fragrance materials to give perfumers new materials to develop new fragrance products.

SUMMARY OF THE INVENTION

The present invention is directed to the compounds of the formula:

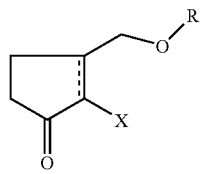

where the dotted line represents a possible double bond; R is selected from the group consisting of methyl and ethyl; and X is selected from the group consisting of $C_1$–$C_7$ moieties and the use of these materials as a fragrance chemical to enhance fragrance in perfumes, toilet waters, colognes, personal products and the like.

More specifically, the present invention is a method for enhancing a perfume by incorporating an olfactory acceptable amount of the compounds set forth above.

These and other embodiments of the present invention will be apparent by reading the following specification.

DETAILED DESCRIPTION OF THE INVENTION

Those with skill in the art readily appreciate the $C_1$–$C_7$ hydrocarbon moiety attached to the ring. The hydrocarbon moiety can be straight, branched, or cyclic as well as saturated or unsaturated hydrocarbons.

Representative moieties include alkyl groups such as but not limited to $CH_3C_2H_5$, $C_4H_9C_5H_{11}$; $CH(CH_3)CH_2CH_2CH_3$; $CH_2CH(CH_3)CH_2CH_3$ and $CH_2CH_2CH(CH_3)CH_3$; cyclobutyl, cyclopentyl; as well as unsaturated moieties including but not limited to: $CH=CHCH_2CH_2CH_3$; $CH_2CH=CHCH_2CH_3$; $CH_2CH_2CH=CHCH_3$; and $CH=C(CH_3)CH_2CH_3$. Those with skill in the art will appreciate that the present invention includes various isomers, which are contemplated within the scope of the present invention.

The present invention is also directed to the use of these compounds in fragrance formulations.

In a highly preferred embodiment, the present invention is directed to the novel compounds, 3-(methoxymethyl)-2-pentylcyclopent-2-en-1-one as depicted below:

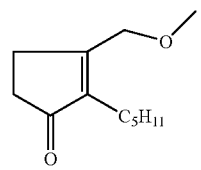

and 3-(methoxymethyl)-2-pentylcyclopenta-1-one:

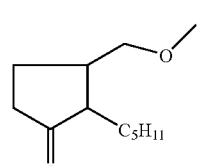

In a highly preferred embodiment of the invention, we have discovered that 3-(methoxymethyl)-2-pentylcyclopenta-1-one has a powerful, white floral odor, reminiscent of magnolia flower and jasmine combined with a light, creamy undertone. When tested on blotters, the fragrance had a good substantivity on test blotters. Similarly, 3-(methoxy-methyl)-2-pentylcyclopent-2-en-1-one has a strong, white floral odor, reminiscent of lily of the valley and magnolia flower. The top note is slightly greener compared to 3-(methoxymethyl)-2-pentylcyclopenta-1-one, but has also the attractive, creamy undertone. Substantivity on blotters is also excellent.

The compounds of the present invention are described in greater detail in the Examples below. The generic reaction sequence involves the reaction of the starting material such as 2-pentyl 2-cyclopentenone, with nitromethane or nitroethane as appropriate, preferably in the presence of sodium methoxide, to form the corresponding nitromethyl cylcopentanone compound, such as 3-(nitromethyl)-2-pentylcyclopentanone. The sodium salt of the compound is then prepared from the corresponding nitro compound through the reaction with sodium methoxide. The sodium salt product is then refluxed with toluene and phosphoric acid to provide the unsaturated compounds of the present invention. The corresponding saturated compounds are prepared by the hydrogenation of the compound using a palladium catalyst at pressures of about 200 pounds per square inch and temperatures of 100° C.

The use of the compounds of the present invention is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compounds of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk flower scents such as lavender-like, rose-like, iris-like, and carnation-like. Other pleasant scents include herbal and woodland scents derived from pine, spruce other forest smells. Fragrances may also be derived from various oils, such as essential oils, or from plant materials such as peppermint, spearmint and the like.

A list of suitable fragrances is provided in U.S. Pat. No. 4,534,891. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compounds of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art, without departing from the scope of this invention. As used herein, in both the specification and following examples, all percentages are weight percent unless noted to the contrary. IFF as used in the examples is understood to mean International Flavors & Fragrances Inc., and DPG is understood to mean dipropylene glycol.

EXAMPLE 1

SYNTHESIS OF 3-(METHOXYMETHYL)-2-PENTYLCYCLOPENT-2-EN-1-ONE AND 3-(METHOXY)-2-PENTYLCYCLOPENTA-1-ONE

Three hundred grams of commercially available 2-pentyl 2-cyclopentenone in 300 ml of methanol was added to a mixture of 180 grams of nitromethane and 180 grams of sodium methoxide at 0° C. in a 3 liter reactor equipped with a stirrer. The reaction was allowed to take place for about three hours. After aging, the reaction mixture was quenched with 75 grams of acetic acid. The reaction mixture was added to 2 liters of a 1/1 mixture of water/toluene. The organic layer was separated and distilled to provide 3-(nitromethyl) 2-pentycylopentanone in quantitative yield.

The sodium salt of 3-(nitromethyl) 2-pentycylopentanone (1 mole) was prepared from the corresponding nitro compound and sodium methoxide. The nitro salt in 5 liters of methanol was added to a 1M solution of HCl at room temperature. The reaction was stirred one hour and poured into ice water (2 L) containing 1 liter of toluene. The toluene layer was separated and washed with water, (2×500 ml). The toluene was removed by Rot-o-Vap to provide crude 3-(dimethoxy-methyl)-2-pentylcyclopentanone which is used in the next step of the synthesis of the compounds.

PROCESS FOR MANUFACTURE OF 3-(METHOXYMETHYL)-2-PENTYLCYCLOPENT-2-EN-1-ONE 3-(dimethoxymethyl)-2-pentylcycylopentan-1-one (0.5 mol), toluene 250 ml and phosphoric acid (0.01 mol) were charged in a reaction flask and heated to reflux for 48 hrs. The reaction mixture was cooled to room temperature and washed with 5% sodium bicarbonate. Distillation of the washed reaction crude provided 3-(methoxymethyl)-2-pentylcyclopent-2-en-1-one having the following spectra:

$^1$HNMR (ppm): 0.85 (triplet, 3H), 1.3 (multiplet, 6H), 2.15 (triplet, 2H), 2.35 (triplet, 2H), 2.6 (triplet, 2H), 3.35 (singlet, 3H), 4.25 (singlet, 2H).

PROCESS FOR MANUFACTURE OF 3-(METHOXYMETHYL)-2-PENTYLCYCLOPENTA-1-ONE

Using a standard autoclave pressure reactor 3-(methoxymethyl)-2-pentylcyclopent-2-en-1-one (0.5 mol) was hydrogenated at 100° C. and 200 pounds per square inch using 5% palladium on carbon as a catalyst. After filtration, 3-(methoxymethyl)-2-pentylcyclopentan-1-one was obtained as was confirmed by the following data;

$^1$HNMR (ppm): 0.90 (triplet, 3H), 1.3 (multiplet, 6H), 1.60 (multiplet, 3H), 1.95 (multiplet, 1H), 2.15 (multiplet, 3H), 2.35 (multiplet, 1H), 3.40 (singlet, 3H), 3.45 (doublet of doublet, 2H).

EXAMPLE 2

Use of the Novel Compounds as Fragrance Materials

The novel compounds of the present invention were used in the following fragrance formulation.

| GREEN TEA | 3-(methoxy-methyl)-2-pentylcyclo-pent-2-en-1-one | 3-(methoxy-methyl)-2-pentylcyclo-penta-1-one |
|---|---|---|
| Bergamot Oil Italy MPF "PFG" | 20.00 | 20.00 |
| Cardamom Oil Ceylon Ref A LMR | 1.00 | 1.00 |
| Damascenone Firm | 2.00 | 2.00 |
| Dipropylene Glycol | 18.00 | 18.00 |
| Helional | 66.00 | 66.00 |

-continued

| GREEN TEA | 3-(methoxy-methyl)-2-pentylcyclo-pent-2-en-1-one | 3-(methoxy-methyl)-2-pentylcyclo-penta-1-one |
|---|---|---|
| Hexenol, B, Gamma Extra 10% DPG | 2.00 | 2.00 |
| Ionone Beta Extra | 30.00 | 30.00 |
| 3-(methoxymethyl)-2-pentylcyclopent-2-en-1-one | 120.00 | — |
| Jasmone Cis 10% DPG | 65.00 | 65.00 |
| Linalool Syn | 26.00 | 26.00 |
| 3-(methoxymethyl)-2-pentylcyclopenta-1-one | — | 120.00 |
| TOTAL | 350.00 | 350.00 |

The Green Tea formula containing 3-(methoxymethyl)-2-pentylcyclopent-2-en-1-one has a greener, more citrus top note than the formula containing 3-(methoxymethyl)-2-pentylcyclopenta-1-one, which has more floral and less citrus character.

What is claimed is:

1. A method for improving, enhancing or modifying a fragrance through the addition of an olfactory acceptable amount of the compound having the structure:

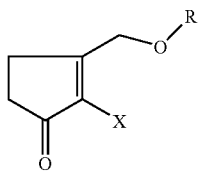

where:
R is selected from methyl and ethyl; and
X is a $C_1$–$C_7$ hydrocarbon moiety.

2. The method of claim 1 through the addition of an olfactory acceptable amount of a fragrance chemical 3-(methoxymethyl)-2-pentylcyclopent-2-en-1-one.

3. The method of claim 1 wherein the fragrance is incorporated into a product selected from perfumes, colognes, candles, toilet waters, cosmetic products, personal care products, fabric care products, cleaning products and air fresheners.

4. The method of claim 2 wherein the cleaning product is selected from the group consisting of soaps, detergents, dishwashing compositions, scrubbing compounds and window cleaners.

5. The method of claim 2 wherein the product is a personal care product.

6. The method of claim 1 wherein the level of the fragrance chemical is from about 0.005 to about 10 weight percent.

7. The method of claim 1 wherein the level of fragrance chemical is from about 0.1 to about 8 weight percent.

8. The method of claim 1 wherein the level of fragrance chemical is from about 0.5 to about 5 weight percent.

9. The compound having the structure:

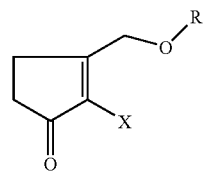

where:
R is selected from methyl and ethyl; and
X is a $C_1$–$C_7$ hydrocarbon moiety.

10. The compound of claim 9 selected wherein the compound is 3-(methoxymethyl)-2-pentylcyclopent-2-en-1-one.

11. A composition comprising a product selected from the group consisting of perfumes, colognes, candles, toilet waters, cosmetic products, personal care products, fabric care products, cleaning products and air fresheners and an olfactory effective amount of the compound of claim 9.

12. The composition of claim 11 wherein the compound is 3-(methoxymethyl)-2-pentylcyclopent-2-en-1-one.

* * * * *